United States Patent
Ling et al.

(10) Patent No.: US 11,435,276 B2
(45) Date of Patent: Sep. 6, 2022

(54) MEDIUM EVALUATION METHOD, MEDIUM, AND CULTURE METHOD

(71) Applicant: FUJIFILM CORPORATION, Tokyo (JP)

(72) Inventors: Xiao Ling, Kanagawa (JP); Kiyokazu Hashimoto, Kanagawa (JP); Haruki Tomikawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 811 days.

(21) Appl. No.: 16/364,186

(22) Filed: Mar. 26, 2019

(65) Prior Publication Data

US 2019/0219492 A1 Jul. 18, 2019

Related U.S. Application Data

(63) Continuation of application No. PCT/JP2017/033606, filed on Sep. 15, 2017.

(30) Foreign Application Priority Data

Sep. 30, 2016 (JP) .............................. JP2016-195053

(51) Int. Cl.
| | |
|---|---|
| G01N 15/04 | (2006.01) |
| G01N 27/72 | (2006.01) |
| G01N 33/50 | (2006.01) |
| G01N 15/00 | (2006.01) |

(52) U.S. Cl.
CPC ............. G01N 15/04 (2013.01); G01N 27/72 (2013.01); G01N 33/5005 (2013.01); G01N 2015/0042 (2013.01)

(58) Field of Classification Search
None
See application file for complete search history.

(56) References Cited

U.S. PATENT DOCUMENTS

| | | |
|---|---|---|
| 2005/0054101 A1 | 3/2005 | Felder et al. |
| 2009/0197329 A1 | 8/2009 | Lee et al. |
| 2017/0009201 A1 | 1/2017 | Hayashi et al. |

FOREIGN PATENT DOCUMENTS

| | | |
|---|---|---|
| CN | 101416059 A | 4/2009 |
| CN | 105934511 A | 9/2016 |
| JP | 2016-099238 A | 5/2016 |

(Continued)

OTHER PUBLICATIONS

International Search Report issued in International Application No. PCT/JP2017/033606 dated Dec. 5, 2017.

(Continued)

*Primary Examiner* — Daniel S Larkin
(74) *Attorney, Agent, or Firm* — SOLARIS Intellectual Property Group, PLLC (57) ABSTRACT

Provided is a medium evaluation method for evaluating the suitability of a medium in which cell aggregates are cultured in a suspended state, by which an evaluation of whether a medium is adequate for both the cell retention performance and the cell recovery efficiency, the medium evaluation method including dispersing a plurality of particles in a medium, measuring a sedimentation velocity by which the particles settle in the medium, and using the sedimentation velocity thus measured as an index value indicating the suitability of the medium; and also provided are a medium and a culture method.

8 Claims, 6 Drawing Sheets

(56) References Cited

FOREIGN PATENT DOCUMENTS

WO          2004/078961  A1      9/2004
WO          2015/111686  A1      7/2015

OTHER PUBLICATIONS

Written Opinion of the ISA issued in International Application No. PCT/JP2017/033606 dated Dec. 5, 2017.
Extended European Search Report dated Jul. 25, 2019, issued in corresponding EP Patent Application No. 17855802.9.
English language translation of the following: Office action dated Feb. 4, 2020 from the JPO in a Japanese patent application No. 2018-542410 corresponding to the instant patent application.
English language translation of the following: Office action dated Apr. 24, 2022 from the SIPO in a Chinese patent application No. 201780060847.0 corresponding to the instant patent application. This office action translation is submitted now in order to supplement the understanding of the cited references which are being disclosed in the instant Information Disclosure Statement.

MEDIUM EVALUATION METHOD, MEDIUM, AND CULTURE METHOD

CROSS-REFERENCE TO RELATED APPLICATIONS

This application is a continuation application of International Application No. PCT/JP2017/033606, filed Sep. 15, 2017, the disclosure of which is incorporated herein by reference in its entirety. Further, this application claims priority from Japanese Patent Application No. 2016-195053, filed Sep. 30, 2016, the disclosure of which is incorporated herein by reference in its entirety.

BACKGROUND

1. Technical Field

The disclosed technology relates to a medium evaluation method, a medium, and a culture method.

2. Related Art

Generally, culture methods referred to as so-called three-dimensional culture, by which cell aggregates (cells) are cultured in a suspended state, are known. It is known that the medium used for the three-dimensional culture is such that even in a case in which a medium is produced using similar processes, a variation in the cell aggregates retention performance or the recovery efficiency for cell aggregates occurs as a result of a slight variation in the conditions. Therefore, for a medium, it is desirable to evaluate the cell aggregates retention performance or the recovery efficiency for cell aggregates. However, the variation in the retention performance or recovery efficiency is very small, and it may be difficult to directly measure the retention performance or the recovery efficiency.

In this regard, for example, a technology for evaluating a medium based on the sedimentation velocity of iron spheres introduced into a medium is described in WO2004/078961A. In WO2004/078961A, it is described that in a case in which the sedimentation velocity of the iron spheres is fast, cells are likely to sediment in the medium during culture, that is, the retention performance is enhanced; whereas in a case in which the sedimentation velocity of the iron spheres is slow, the operation for recovering cells becomes difficult, that is, there is a possibility that the recovery efficiency may decrease. Furthermore, in WO2004/078961A, it is described that in order to avoid sedimentation of cells, the medium should have appropriate specific gravity and viscosity.

SUMMARY

In conventional technologies, the retention performance or recovery efficiency for cell aggregates in a medium is evaluated from a viewpoint based on the viscosity of the medium. However, there have been occasions in which only from the viewpoint of the viscosity of the medium, the retention performance or recovery efficiency for cells aggregates in a medium cannot be adequately evaluated. For example, there were media that had identical viscosity but exhibited different retention performance or recovery efficiencies (see Table 1).

Therefore, in order to perform an evaluation on whether a medium is adequate for both the cell retention performance and the cell recovery efficiency, conventional technologies are not satisfactory.

The disclosed technology provides a medium evaluation method that enables an evaluation on whether a medium is appropriate for both the cell retention performance and the cell recovery efficiency; a medium; and a culture method.

A medium evaluation method of a first aspect of the present disclosure is a medium evaluation method for evaluating the suitability of a medium in which cell aggregates are cultured in a suspended state, the method comprising dispersing a plurality of particles in a medium as predetermined particles, measuring a sedimentation velocity at which the predetermined particles settle in the medium, and using the sedimentation velocity thus measured as an index value indicating the suitability of the medium.

A medium evaluation method of a second aspect of the present disclosure is the medium evaluation method according to the first aspect, in which the predetermined particles have a particle size of from 70 μm to 500 μm and a density of 2 g/cm$^3$ or higher, in order to determine whether a retention power for cell aggregates provided by a network structure produced by various polymers in the medium is in a range of the suitability.

A medium evaluation method of a third aspect of the present disclosure is the medium evaluation method according to the first aspect or the second aspect, in which the medium in which the predetermined particles have a particle size of 200 μm and a density of 2.5 g/cm$^3$, and the index value is in the range of from 1.0 mm/s to 4.0 mm/s, which is predetermined range, is determined as an adequate medium.

A medium evaluation method of a fourth aspect of the present disclosure is the medium evaluation method according to the first aspect or the second aspect, in which the medium in which the predetermined particles have a particle size of 200 μm and a density of 2.5 g/cm$^3$, and the index value is in the range of from 2.5 mm/s to 4.0 mm/s, which is predetermined range, is determined as an adequate medium.

A medium evaluation method of a fifth aspect of the present disclosure is the medium evaluation method according to the third aspect or the fourth aspect, in which an upper limit of the predetermined range is a value that has been predetermined based on a retention performance by which a medium retains the cell aggregates during culture.

A medium evaluation method of a sixth aspect of the present disclosure is the medium evaluation method according to any one of the third aspect to the fifth aspect, in which a lower limit of the predetermined range is a value that has been predetermined based on a recovery efficiency by which cell aggregates are recovered from a medium.

A medium of a seventh aspect of the present disclosure is a medium having an index value of from 1.0 mm/s to 4.0 mm/s, which is derived by a medium evaluation method, in which the medium evaluation method is a medium evaluation method for evaluating the suitability of a medium for culturing cell aggregates in a suspended state, the method including introducing particles having a particle size of 200 μm and a density of 2.5 g/cm$^3$ into the medium, measuring a sedimentation velocity at which the particles settle in the medium, and using the sedimentation velocity thus measured as an index value indicating the suitability of the medium.

A medium of an eighth aspect of the present disclosure is a medium having an index value of from 2.5 mm/s to 4.0 mm/s, which is derived by a medium evaluation method, in which the medium evaluation method is a medium valuation method for evaluating the suitability of a medium for culturing cell aggregates in a suspended state, the method including introducing particles having a particle size of 200 µm and a density of 2.5 g/cm³ into the medium, measuring a sedimentation velocity at which the particles settle in the medium, and using the sedimentation velocity thus measured as an index value indicating the suitability of the medium.

A culture method of a ninth aspect of the present disclosure comprises culturing cell aggregates by three-dimensional culture using the medium according to the seventh aspect or the eighth aspect.

Furthermore, a medium evaluation method of a tenth aspect of the present disclosure is a medium evaluation method for evaluating the suitability of a medium in which cell aggregates are cultured in a suspended state, the method comprising dispersing a plurality of magnetic particles in a medium contained in a container, measuring a predetermined distance x in which the number ratio of the particle numbers obtained before and after the application of a magnetic field of the magnetic particles included in the range of a predetermined region starting from a predetermined distance from the source of magnetic field generation, is a predetermined value, and using the distance x thus measured as an index value indicating the suitability of the medium.

A medium evaluation method of an eleventh aspect of the present disclosure is the medium evaluation method according to the tenth aspect, in which the range of the predetermined region is the range of from 3 times to 100 times the particle size of the magnetic particles.

A medium evaluation method of a twelfth aspect of the present disclosure is the medium evaluation method according to the tenth aspect or the eleventh aspect, in which magnetic polylactic acid particles having a particle size of 100 µm, a density of 1.4 g/cm³, and a magnetite percentage content of 40% are used as the magnetic particles.

A medium evaluation method of a thirteenth aspect of the present disclosure is the medium evaluation method according to any one of the tenth aspect to the twelfth aspect, in which the application of a magnetic field is carried out by disposing a magnet having a surface magnetic flux density of from 150 mT to 250 mT on a predetermined unidirectional surface of the container.

A medium evaluation method of a fourteenth aspect of the present disclosure is the medium evaluation method according to the tenth aspect or the eleventh aspect, in which magnetic polylactic acid particles having a particle size of 100 µm, a density of 1.4 g/cm³, and a magnetite percentage content of 40% are used as the magnetic particles, the application of a magnetic field is carried out by disposing a magnet having a surface magnetic flux density of 200 mT on a predetermined unidirectional surface of the container, and the medium having an index value thus measured in a predetermined range is determined as an adequate medium.

A medium evaluation method of a fifteenth aspect of the present disclosure is the medium evaluation method according to the fourteenth aspect, in which an upper limit of the predetermined range is a value that has been predetermined based on a retention performance by which a medium retains the cell aggregates.

A medium evaluation method of a sixteenth aspect of the present disclosure is the medium evaluation method according to the fourteenth aspect or the fifteenth aspect, in which a lower limit of the predetermined range is a value that has been predetermined based on a recovery efficiency of recovering cell aggregates from a medium.

A medium of a seventeenth aspect of the present disclosure is a medium having an index value of from 4 mm to 8 mm, which is derived by a medium evaluation method for evaluating the suitability of a medium for culturing cell aggregates in a suspended state, the method including dispersing a plurality of magnetic particles that use magnetic polylactic acid particles having a particle size of 100 µm, a density of 1.4 g/cm³, and a magnetite percentage content of 40% in the medium contained in a container, measuring a predetermined distance x in which the number ratio of the particle numbers obtained before and after the application of a magnetic field of the magnetic particles included in the range of a predetermined region starting from a predetermined distance from the source of magnetic field generation, which is a magnet disposed on a predetermined unidirectional surface of the container and having a surface magnetic flux density of 200 mT, is 0.5, and using the distance x thus measured as an index value indicating the suitability of the medium, in which the medium is determined as an adequate medium.

A culture method of an eighteenth aspect of the present disclosure comprises culturing cell aggregates by three-dimensional culture using the medium according to the seventeenth aspect.

A medium of a nineteenth aspect of the present disclosure has an index value, which is a sedimentation velocity derived by the medium evaluation method according to the second aspect, of 1 mm/s or greater, and has an index value, which is distance x derived by the medium evaluation method according to the fourteenth aspect, of 10 mm or less.

A medium of a twentieth aspect of the present disclosure has an index value, which is a sedimentation velocity derived by the medium evaluation method according to the second aspect, of from 4 mm/s to 12 mm/s, and has an index value, which is distance x derived by the medium evaluation method according to the fourteenth aspect, of 5 mm or less.

According to the present disclosure, an evaluation of whether a medium is adequate for both the cell retention performance and the cell recovery efficiency is made possible.

BRIEF DESCRIPTION OF THE DRAWINGS

Exemplary embodiments according to the technique of the present disclosure will be described in detail based on the following figures, wherein.

DETAILED DESCRIPTION

The technology of the present disclosure is a technology related to an evaluation method for evaluating the suitability of a medium used for three-dimensional culture of cell aggregates. Three-dimensional culture is a technology for culturing cells in a medium in a suspended state, and has a feature that high quality cells can be stably supplied in large quantities compared to conventional two-dimensional culture (adhesion culture).

It is preferable for a medium used for three-dimensional culture that in the case of stabilizing suspension of cell aggregates and performing a concentration treatment and the like, separation between cell aggregates and the medium can be easily achieved. Therefore, in the technology of the present disclosure, as the suitability of the medium, the viewpoints of the cell aggregates retention performance and the recovery efficiency for cell aggregates are evaluated. Meanwhile, the "retention performance" is a performance of retaining cell aggregates in a medium, and superior retention performance implies that even in a case in which cells grow and proliferate in the course of cell culture, the cells do not precipitate or fuse with one another. Therefore, it is preferable that the retention performance is superior. Furthermore, the "recovery efficiency" is the cell recovery efficiency (number of separated cells/number of cells included in the medium) at the time of separating only the cells in the medium, and as the recovery efficiency is higher, the cells can be easily recovered. Therefore, it is preferable that the recovery efficiency is higher. Meanwhile, as the retention performance is superior, it is more difficult for cells to be separated from the medium, and therefore, the recovery efficiency may decrease.

According to the technology of the present disclosure, examples of the "cell aggregates" are aggregates of common cells; aggregates of stem cells or aggregates of differentiated somatic cells, or aggregates of those stem cells and differentiated somatic cells existing as a mixture; and aggregates of induced pluripotent stem (iPS) cells. Meanwhile, according to the technology of the present disclosure, in the case of evaluating the suitability of a medium for culturing cell aggregates having a size of about 70 μm to 500 μm, an evaluation can be carried out with higher accuracy.

Furthermore, in the following description, "cell aggregates" may be simply referred to as "cells".

Generally, evaluation methods based on viscosity are known as methods for evaluating a medium; however, there have been occasions in which media used for three-dimensional culture have identical viscosity but different retention performance.

In Table 1, for each of Medium I, Medium II, and Medium III, the viscosity, the sedimentation velocity obtained in a case in which small beads (particles) having a particle size of 200 μm and a density of 2.5 g/cm³ are dispersed, the sedimentation velocity obtained in a case in which large beads (particles) having a particle size of 1 mm and a density of 6 g/cm³ are dispersed, and the cell retention performance, are shown. In the cases that are shown in Table 1, for the cell retention performance, a sensory evaluation by visual inspection of the retention performance for cell aggregates is performed. The retention performance of Medium I is denoted as "A", and in a case in which the retention performance is equal or superior to that of Medium I, the medium is rated as "A", while in a case in which the retention performance is inferior to that of Medium I, the medium is rated as "B".

TABLE 1

|  | Medium I | Medium II | Medium III |
|---|---|---|---|
| Viscosity (viscometer) | 1.2 Pa · s | 1.2 Pa · s | 10 Pa · s |
| Cell retainability (sensory evaluation) | A | B | A |
| Sedimentation velocity small beads (200 μm, 2.5 g/cm³) | 6 mm/s | 25 mm/s | 0.1 mm/s |
| Sedimentation velocity large beads (1 mm, 6 g/cm³) | 100 mm/s | 100 mm/s | 10 mm/s |

As shown in Table 1, Medium I and Medium II have the same viscosity, and while the sedimentation velocity of the small beads (particles) is faster in the case of Medium II, the sedimentation velocity of the large beads (particles) is the same. Furthermore, the retention performance is "A", that is, appropriate, in the case of Medium I; however, the retention performance is "B", that is, inappropriate, in the case of Medium II.

Medium III has higher viscosity compared to Medium I and Medium II, and the sedimentation velocity of the small beads (particles) and large beads (particles) is also slow. The retention performance of Medium III is "A", that is, appropriate.

As such, even in the case in which the viscosities of the media are the same, the sedimentation velocity of particles may be different, and the cell aggregates retention performance may also be different.

In regard to this phenomenon, the present inventors found, as a result of investigation, that cells suspended in a medium do not settle only due to the viscosity resistance of the medium, but also because the cells are retained in a network formed by the polymers added to the medium. The retention power of the network formed by polymers is very small, and it is considered that the retention power is of the extent that holds objects having a size and a density equivalent to those of cells or the like.

Thus, in the technology of the present disclosure, an evaluation of whether a medium is adequate for both the cell retention performance and the cell recovery efficiency is made possible based also on the retention power formed by the polymers added to the medium.

In the following description, embodiments of the technology of the present disclosure will be explained with reference to the drawings. The same reference numerals will be assigned to the same or equivalent constituent elements and parts in the various drawings, and any overlapping descriptions will not be repeated.

First Embodiment

In the present embodiment, the sedimentation velocity of particles dispersed in a medium was measured, and the sedimentation velocity thus measured was used as an index value indicating the suitability of the medium.

Figure 1:
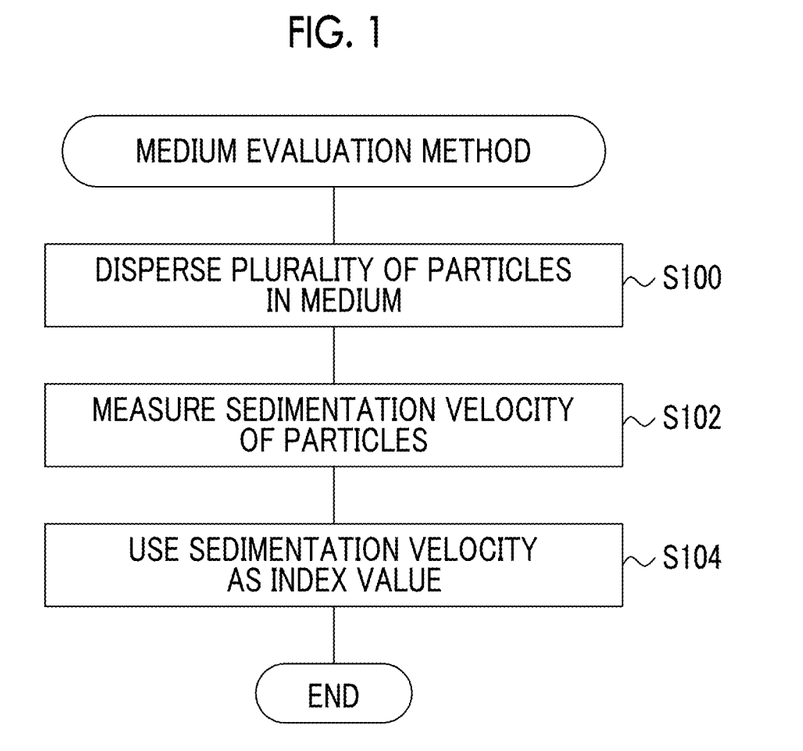
FIG. 1 is a flowchart describing an example of the process flow of a medium evaluation method according to a first embodiment.

FIG. 1 shows a flowchart describing an example of the process flow of the medium evaluation method of the present embodiment.

As shown in FIG. 1, in Step S100, 5 mg of particles were introduced into a transparent container having a size of 10 mm×10 mm×50 mm (length×width×height) and containing 3 ml of a medium, the particles were dispersed by stirring, and then the system was left to stand for one hour at a temperature of 22° C. Here, the height of the container is not particularly limited; however, the height is preferably 50 mm.

Regarding the particles, particles made of soda lime and having a density of 2.5 g/cm$^3$ and a particle size of 200 μm (accuracy: 200±10 μm, standard deviation: 6 or less) (SPL200 manufactured by Unitika, Ltd.) were used.

It is preferable that the particle size of the particles used for the evaluation is equal to the size of cell aggregates, in order to evaluate the retention performance concerning cell aggregates (for example, stem cells) cultured in the medium as an object of evaluation. For example, in the case of stem cells, the size of cell aggregates is about 70 μm to 500 μm, and in a case in which the cell aggregates are smaller than this, the cells undergo cell death, while in a case in which the cell aggregates are larger, the interior of the cell aggregates undergoes necrosis. Therefore, similarly to the present embodiment, the particle size of the particles is preferably from 70 μm to 500 μm, and more preferably 200 μm.

The density of the particles used for the evaluation is preferably a density corresponding to cell aggregates cultured by means of the medium as an object of evaluation, and due to the reasons described in detail below, the density of the particles is preferably about two or more times the density of the cell aggregates. For example, in the case of iPS cells, since the density of the cell aggregates is 1.1 g/cm$^3$ or greater, in the above example, the density of the cell aggregates is preferably 2 g/cm$^3$ or greater, and more preferably 2.5 g/cm$^3$ or greater.

Furthermore, since the variations in the density and particle size of the particles lead to variations in the measurement results, it is preferable that the particles used for the evaluation have a uniform density and a uniform particle size as far as possible. In the present embodiment, particles having a standard deviation of 6 or less were used. Since the sedimentation velocity is directly proportional to the square of the particle size, in order to maintain the weight variation accuracy, it is preferable that the variation of the particle size as a range that does not affect the measurement accuracy is ±10%.

It is preferable that the quantity of the particles to be introduced into the medium is small; however, in a case in which the number of the particles is small, the N number is small (the number of samples is small). Meanwhile, in a case in which the quantity of the particles is large, the particles affect one another during sedimentation, and thereby the sedimentation velocity thus measured may become inaccurate. Therefore, it is preferable that the number of particles is 5 mg (in the case of a density of 2.5 g/cm$^3$ and a particle size of 200 μm), as is the case of the present embodiment.

In the subsequent Step S102, the sedimentation velocity of the particles is measured. In the present embodiment, before the sedimentation velocity is measured, first, 1 ml of the medium in a state of having particles dispersed therein is suctioned and returned using a pipette, and thereby the medium is stirred (about 1 ml/mm$^2$.s).

Figure 2:
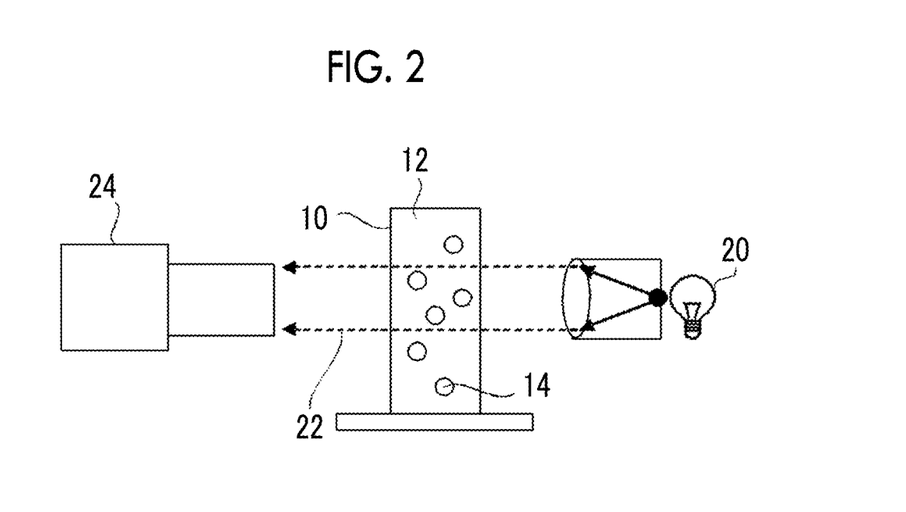
FIG. 2 is an explanatory diagram for explaining a method for imaging the state of particles settling in the evaluation method according to the first embodiment.

Then, as explained above, the state in which convection of the stirred medium subsided and the particles settled in the medium at a constant velocity, was imaged. In the present embodiment, as illustrated in FIG. 2 as an example, a container 10 containing a medium 12 having the particles 14 dispersed therein is irradiated with parallel light 22 coming from a light source 20, and imaging is performed using a camera 24 under the conditions of 30 fps as a moving image.

In the present embodiment, the operation of combining stirring of the medium and imaging of the state of the particles settling in the medium is carried out repeatedly for 5 or more times (about 20 times at the most).

In a case in which the stirring conditions are too severe, such as the speed of stirring the medium is fast, the network of the network structure held by the medium is destroyed, and the sedimentation velocity becomes fast. On the other hand, in a case in which the stirring conditions are too mild, such as the speed of stirring the medium is slow, since the particles are not sufficiently whirled up, there is a risk that the sedimentation velocity may not be accurately measured. Therefore, it is necessary that the quantity and speed of stirring do not vary from measurement to measurement.

From the moving image taken as such, the portion in which the particles gently settle is defined, and the quantity of movement and the time of movement of the particles are derived by an image analysis. Thus, the average sedimentation velocity of individual particles is derived. Furthermore, the average value of the sedimentation velocities of 50 to 100 particles is derived for stirring of one time, and the average value is used as the sedimentation velocity of that round. Furthermore, the average value of the sedimentation velocities of several times (at least five or more times are needed) was derived, and the average value derived therefrom was used as the sedimentation velocity of the particles settling in the medium.

In the subsequent Step S104, the sedimentation velocity is used as an index value, and thereby, the evaluation according to the medium evaluation method of the present embodiment is completed.

In regard to the medium for which the sedimentation velocity as an index value for evaluating the suitability of the medium by the above-described evaluation method, cell aggregates were actually introduced into the medium, and the retention performance and the recovery efficiency were evaluated. In regard to the retention performance, an evaluation is carried out on the settled state of cells as "floatability", and an evaluation was carried out on the fusion or precipitation of cells as "culturing".

Regarding the medium as an object of evaluation, a medium prepared by adding gel-forming suspended carriers (Mebiol, cellulose nanofibers, gellan gum, methyl cellulose, and the like) and a thickening agent to a water-degradable maintenance medium, was used. Furthermore, an evaluation was carried out for three kinds of media (media 1, 2, and 3) that included the same components and had no significant differences in viscosity or the like, but were produced by different production processes or the like. The concentrations of the components of the media were varied according to the size of the cell aggregates used for the evaluation. In a case in which the size of the cell aggregates was 120 μm or larger, media (media 1, 2, and 3) having high concentrations (composition called Medium 2) were used, and in a case in which the size of the cell aggregates was smaller than the above-described value (80 μm or larger and smaller than 120 μm), media (media 1#, 2#, and 3#) having low concentrations (composition called Medium 1) were used. Cellulose nanofibers as a gel-forming material were added to mTesR1, which is a general maintenance medium, at a proportion of 0.025% (weight ratio) for Medium 1, and at a proportion of 0.05% (weight ratio) for Medium 2.

The results obtained by performing the evaluation using cell aggregates having a size of 120 μm or larger are presented in Table 2. Furthermore, the results obtained by performing the evaluation using cell aggregates having a size of 80 μm or larger and smaller than 120 μm are presented in Table 3.

TABLE 2

| Medium composition Medium 2 | | Particle density [g/cm³] | | | Evaluation using cells | | Recovery ratio |
|---|---|---|---|---|---|---|---|
| | | I 1.2 | II 2.5 | III 6.0 | Floatability | Culturing | |
| Sedimentation velocity [mm/s] | Medium 1 | X | 1.3 | 3.1 | A | A | A |
| | Medium 2 | X | 0.24 | 0.58 | A | A | B |
| | Medium 3 | 1.9 | 4.4 | 11(Y) | B | B | Z |

TABLE 3

| Medium composition Medium 2 | | Particle density [g/cm³] | | | Evaluation using cells | | Recovery ratio |
|---|---|---|---|---|---|---|---|
| | | I 1.2 | II 2.5 | III 6.0 | Floatability | Culturing | |
| Sedimentation velocity [mm/s] | Medium 1# | X | 3.0 | 7.2 | A | A | A |
| | Medium 2# | X | 2.3 | 5.5 | A | A | B |
| | Medium 3# | 3.0 | 5.3 | 12(Y) | B | B | Z |

In Table 2 and Table 3 described above, the results for an evaluation of the particles having a density of 2.5 g/cm³, which have been mentioned above as particles II and have a density about twice the density of the cell aggregates used for the evaluation, are described. In Table 2 and Table 3, measurement results obtained by measuring the sedimentation velocity of particles I and particles III as particles having densities different from that of the particles II (other conditions are the same) in the same manner as in the medium evaluation method described above (see FIG. 1), are also described. Particles I are particles made of an acrylic resin and having a density of 1.2 g/cm³, which is about the same as the density of the cell aggregates used for the evaluation. Particles II are particles made of zirconia and having a density of 6.0 g/cm³, which is five or more times the density of the cell aggregates used for the evaluation.

"X" in Table 2 and Table 3 implies that since the particles did not settle (precipitate), the sedimentation velocity could not be measured. Furthermore, "(Y)" in Table 2 and Table 3 implies that in a case in which the sedimentation velocity was higher than 10 mm/s, since there is a risk that the sedimentation velocity after the particles suspended by stirring have finished settling before the particles are subjected to convection may not be accurately measured, inaccurate data were obtained. Furthermore, "Z" in Table 2 and Table 3 implies that since the medium was a medium incapable of culture, the recovery ratio could not be evaluated.

In regard to the evaluation of floatability, culture, and recovery ratio, in a case in which a medium was appropriate (highly suitable) for the culture of cell aggregates, the medium was rated as "A"; and in a case in which a medium was not appropriate (less suitable) for the culture of cell aggregates, the medium was rated as "B". Specifically, each medium was rated as "A" or "B" as follows.

In the evaluation of floatability, cell aggregates were dispersed in a medium at a temperature of 37° C., and in a case in which 50% or more of the cell aggregates did not precipitate within 24 hours, the medium was rated as "A", while in a case in which 50% or more of the cell aggregates precipitated, the medium was rated as "B". Here, precipitation means a state in which dispersed cell aggregates have settled at a position of 1 mm or less from the bottom of the container.

In the evaluation for culture, cell aggregates were cultured in a medium under the conditions of a temperature of 37° C. and 5% of $CO_2$, and in a case in which the cell aggregates had proliferated without undergoing fusion or precipitation until the medium exchange after 48 hours, the medium was rated as "A", while in a case in which fusion or precipitation had occurred, and the cell aggregates did not proliferate, the medium was rated as "B". According to the present embodiment, "fusion" is a state in which adjacent cell aggregates unite with one another, and whether fusion has occurred was determined by making a microscopic observation. In a case in which five or more fusion products were confirmed in 3 ml of the medium, the medium was rated as "B".

On the occasion of evaluating the recovery ratio, in a case in which the size of the cell aggregates was 80 μm to 120 μm, recovery was carried out by diluting the cell-including medium five times, centrifuging the dilution at 180 g for 3 minutes, and discarding the supernatant. In a case in which the size of the cell aggregates was 120 μm or larger, recovery was carried out by diluting the cell-including medium five times, centrifuging the dilution at 100 g for 3 minutes, and discarding the supernatant.

In regard to the evaluation of the recovery ratio, in a case in which the recovery efficiency (number of cells that could be recovered/total number of cells in the medium) during the recovery of cells was 80% or higher, the medium was rated as "A"; and in a case in which the recovery efficiency was less than 80%, the medium was rated as "B".

As shown in Table 2 and Table 3, media 1 and 1# exhibited satisfactory results in the evaluation of all of floatability, culturing, and recovery ratio ("A"), while media 2 and 2# exhibited satisfactory results in the evaluation of floatability and culturing ("A") but poor results in the evaluation of the recovery ratio ("B"). This is because since the media 2 and 2# have excessively high retention performance, culturing is possible; however, the recovery ratio is low. Meanwhile, media 3 and 3# exhibited poor results in the evaluation of floatability and culturing ("B"). This is because since the media 3 and 3# have poor retention performance, cells could not be cultured, and therefore, in the evaluation of the recovery ratio, the media were rated as "Z".

As can be seen from Table 2 and Table 3, in a case in which the particles have a particle size of 200 μm and a density of 2.5 g/cm$^3$, a medium having a sedimentation velocity of from 1.0 mm/s to 4.0 mm/s, and more preferably having a sedimentation velocity of from 2.5 mm/s to 4.0 mm/s, can be considered as an adequate medium.

As such, according to the medium evaluation method of the present embodiment, it is possible to evaluate the suitability of the medium by utilizing the sedimentation velocity as an index value. The upper limit of the sedimentation velocity may be determined in advance based on the retention performance of the medium capable of retaining cell aggregates during culture, and the lower limit of the sedimentation velocity may be determined in advance based on the recovery efficiency for recovering cell aggregates.

As shown in Table 2 and Table 3, since Particles I have a low density, the particles do not settle and float in both the media 1 and 2. Therefore, it can be seen that the difference in floatability cannot be evaluated. Meanwhile, Particles III settle in all of the media; however, in a medium having poor results in the evaluation of the retention performance (floatability and culturing), the particles settle too rapidly, and there is a risk that an accurate velocity may not be measured.

Therefore, the density of the particles used for the evaluation is preferably 2 g/cm$^3$ or greater as described above, and when the evaluation system of the present embodiment is considered, the density of the particles is more preferably 2 g/cm$^3$ to 6 g/cm$^3$. However, even in a case in which the density is higher than 6 g/cm$^3$, the evaluation of a medium is possible in principle.

Figure 3:
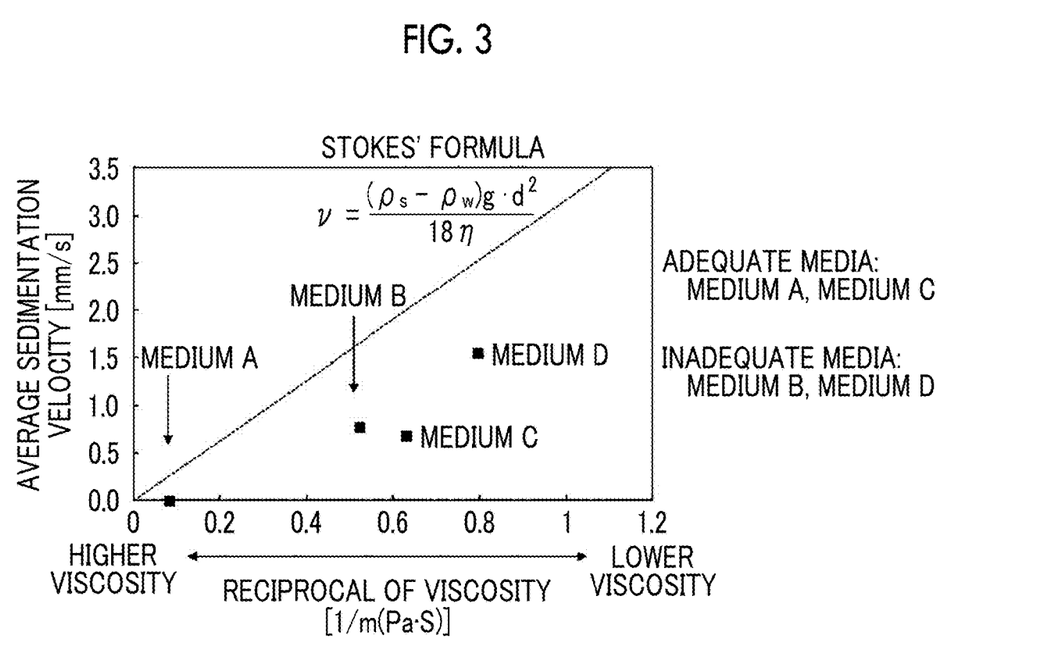
FIG. 3 is a diagram illustrating an example of the correspondence relation between viscosity and the sedimentation velocity that serves as an index value of evaluation, for a medium determined to be appropriate by the evaluation method according to the first embodiment.

For a medium that has been determined to be adequate by the above-mentioned medium evaluation method as such, an example of the correspondence relation between viscosity and the sedimentation velocity that serves as an index value of the evaluation is shown in FIG. 3. In FIG. 3, an example of the correspondence relation between viscosity and the sedimentation velocity is shown for four kinds of dilute media A to D, which have been considered adequate and have gel-forming suspended carriers (Mebiol, cellulose nanofibers, gellan gum, methyl cellulose, and the like) added thereto at a proportion of 0.5% or less. According to FIG. 3, it is understood that medium A and medium C that have been considered to be adequate have slower sedimentation velocities (⅔ or less) than the terminal velocity obtainable by substituting the viscosity (measured value obtained using a viscometer) and density of the medium as well as the particle size and density of the particles into Stokes' Formula (theorem).

As such, in a case in which a medium considered to be adequate does not conform to Stokes' theorem, it is speculated to be because the particles are retained in the network formed by the polymers added to the medium, as described above. As such, regarding an adequate medium, it is preferable that the sedimentation velocity is ⅔ or less of the terminal velocity derived by Stokes' theorem.

As explained above, the medium evaluation method of the present embodiment is a medium evaluation method of evaluating the suitability of a medium for culturing cell aggregates in a suspended state, and the method includes dispersing a plurality of particles in the medium, measuring the sedimentation velocity at which the particles settle in the medium, and using the sedimentation velocity thus measured as an index value indicating the suitability of the medium.

Thereby, an evaluation of whether a medium is adequate for both the cell retention performance and the cell recovery efficiency by considering the influence of the network structure formed by the polymers added to the medium, is made possible.

As cell aggregates are cultured by three-dimensional culture using a medium that has been evaluated to be adequate by the medium evaluation method of the present embodiment, culture of the cell aggregates can be carried out appropriately. In a medium having appropriate retention performance, particles settle slowly; however, in a case in which the retention performance is weak, particles settle rapidly. Furthermore, in a case in which the retention performance is too strong, particles do not settle but stand still. According to the present embodiment, the slight difference in the cell retainability of a medium can be detected with higher sensitivity by selecting the particle size and density of particles.

Second Embodiment

In the present embodiment, an evaluation of the suitability of a medium was carried out using the quantity of movement in a case in which a magnetic field was applied to magnetic particles dispersed in the medium.

Figure 4:
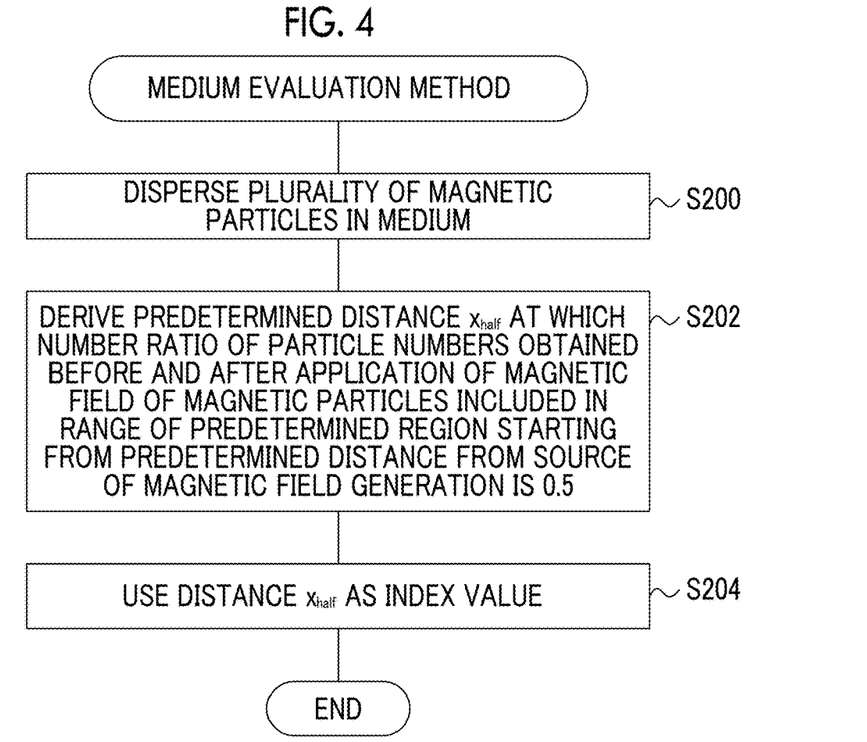
FIG. 4 is a flowchart describing an example of the process flow of a medium evaluation method according to a second embodiment.

FIG. 4 presents a flowchart showing an example of the process flow of the medium evaluation method of the present embodiment.

As shown in FIG. 4, in Step S200, 100 μl of magnetic particles (the density of the particles at the time of measurement was adjusted to 200 to 500 particles/ml) were introduced into a transparent container having a size of 10 mm×10 mm×50 mm (length×width×height) and containing 5 ml of a medium, and the medium was dispersed by stirring. In the present embodiment, magnetic polylactic acid particles (particles manufactured by MicroMod Automation, Inc., PLA-M12-00-105) having a particle size of 100 μm and a density of 1.4 g/cm$^3$ and containing magnetite ($Fe_3O_4$) as a magnetic body at a percentage content of 40% (w/w), were used as an example of the magnetic particles. After the magnetic particles were introduced and stirred, the particles were left to stand for one hour at a temperature of 22° C. As is the case of the standing state schematically illustrated in FIG. 5, in order to disperse the magnetic particles 44 into the medium 42 contained in the container 40 and to bring buoyancy into a stabilized state, it is preferable to leave the system to stand for one hour or longer, similarly to the present embodiment. The temperature during standing and during performing the measurement of the distance x that will be described below is preferably 22° C.

Figure 5:
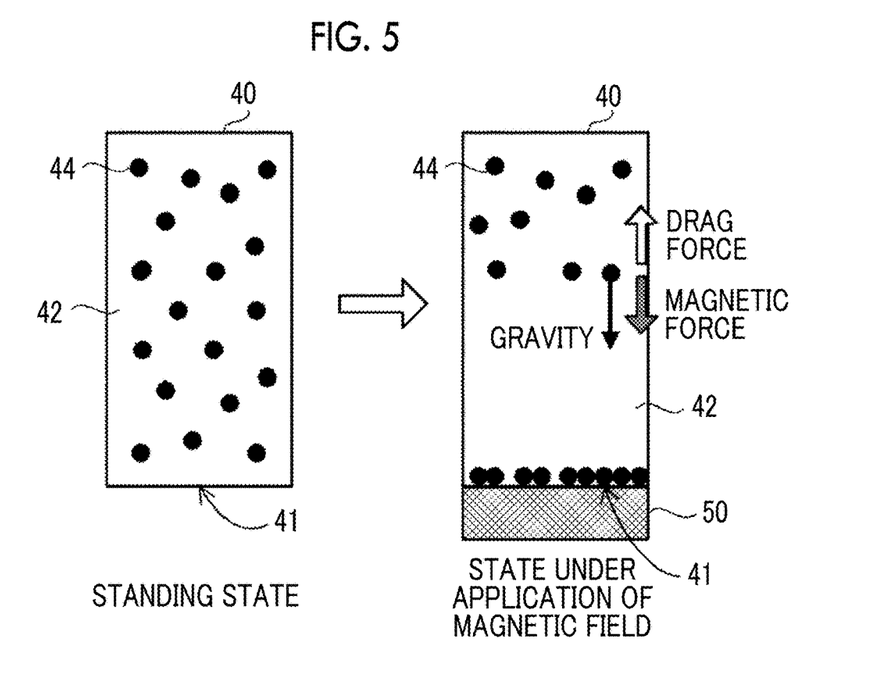
FIG. 5 is an explanatory diagram for explaining the state of magnetic particles before and after the application of a magnetic field in the evaluation method according to the second embodiment.

The size of the container 40 used herein is such that in a case in which the width of the container 40 is wider than the diameter of the magnet 50 serving as a source of magnetic field generation, the magnetic force does not work well. Therefore, it is preferable that the width is narrower than the diameter of the magnet 50.

In the subsequent Step S202, the distance x (equilibrium distance $x_{half}$ that will be described below) at which the ratio of the particle numbers obtained before and after the application of a magnetic field of the magnetic particles 44 included in the range of a predetermined region from a position, the distance from the magnet 40 to the position being a predetermined distance, became 0.5 was derived. As shown in FIG. 5, by applying a magnetic field using the magnet 50 from the bottom face 41 of the container 40, gravity and magnetic force are applied to the magnetic particles 44 in the direction toward the bottom face 41, and a drag force against this is generated.

In the present embodiment, first, before a magnetic field is applied, the container 40 in a standing state is imaged with a camera from sideways, and the dispersed state of the magnetic particles 44 is recorded into an image. Here, the visual field of the image recording the dispersed state is preferably such that the width is greater than or equal to the width of the container (10 mm), and the length is from 20 mm to 50 mm (distance from the bottom face to the top face of the medium 42).

Subsequently, the magnet 50 is disposed on the bottom face 41 of the container 40, and thereby a magnetic field is applied in the container 40. The magnetic particles 44 are attracted to the direction of the magnet 50 for one minute, and then the dispersed state of the magnetic particles 44 is recorded into an image using a camera in the same manner as before the application of the magnetic field. The visual field of the image recording the dispersed state and the dispersed and the scope of imaging in this case are the same as those before the application of a magnetic field. The bottom face 41 of the present embodiment is an example of the predetermined unidirectional surface of the technology of the present disclosure.

Regarding the magnet 50 used for the evaluation, a circular-shaped neodymium magnet having a diameter of 15 mm to 20 mm and a thickness of 2 mm to 3 mm and having a surface magnetic flux density of 200±50 mT was used. The material of the magnet 50 is not particularly limited; however, the surface magnetic flux density is preferably from 150 mT to 250 mT. In a case in which the surface magnetic flux density is 250 mT or less, even though the attractive force caused by a magnetic force becomes strong, the scope of dispersion of the magnetic particles 44 attracted by the magnetic force of the magnet 50 is appropriately suppressed. Therefore, since the viewing angle of the camera used for recording the dispersed state of the magnetic particles 44 can be suppressed from being widened, the suppressed viewing angle can contribute to the size reduction of measuring apparatuses including the above-mentioned camera.

On the other hand, in a case in which the surface magnetic flux density is lower than 150 T, since the quantity of movement of the magnetic particles 44 being attracted by the magnetic force and moving becomes small, errors of measurement are likely to be produced. Therefore, in a case in which the surface magnetic flux density is 150 T or higher, an appropriate quantity of movement of the magnetic particles 44 being attracted by the magnetic force and moving can be secured, and therefore, a decrease in the measurement accuracy can be suppressed.

After the dispersed states of the magnetic particles 44 before the application of a magnetic field and after the application of a magnetic field were recorded into images as such, the medium 42 was stirred as explained above, and the magnetic particles 44 were dispersed. Subsequently, a treatment of recording the dispersed states of the magnetic particles 44 before the application of a magnetic field and after the application of a magnetic field into images was carried out. In the present embodiment, the aforementioned treatment was carried out five times.

The quantity of movement of the magnetic particles is derived by analyzing the images taken before the application of a magnetic field and after the application of a magnetic field. The method of deriving the quantity of movement of the magnetic particles is not particularly limited; however, for example, the following two kinds of methods may be mentioned.

According to a first method, first, an image analysis is performed for a pair of two images obtained before and after the application of a magnetic field, and the distances x of various magnetic particles 44 from the bottom face 41 of the container 40 are derived.

Figure 6:
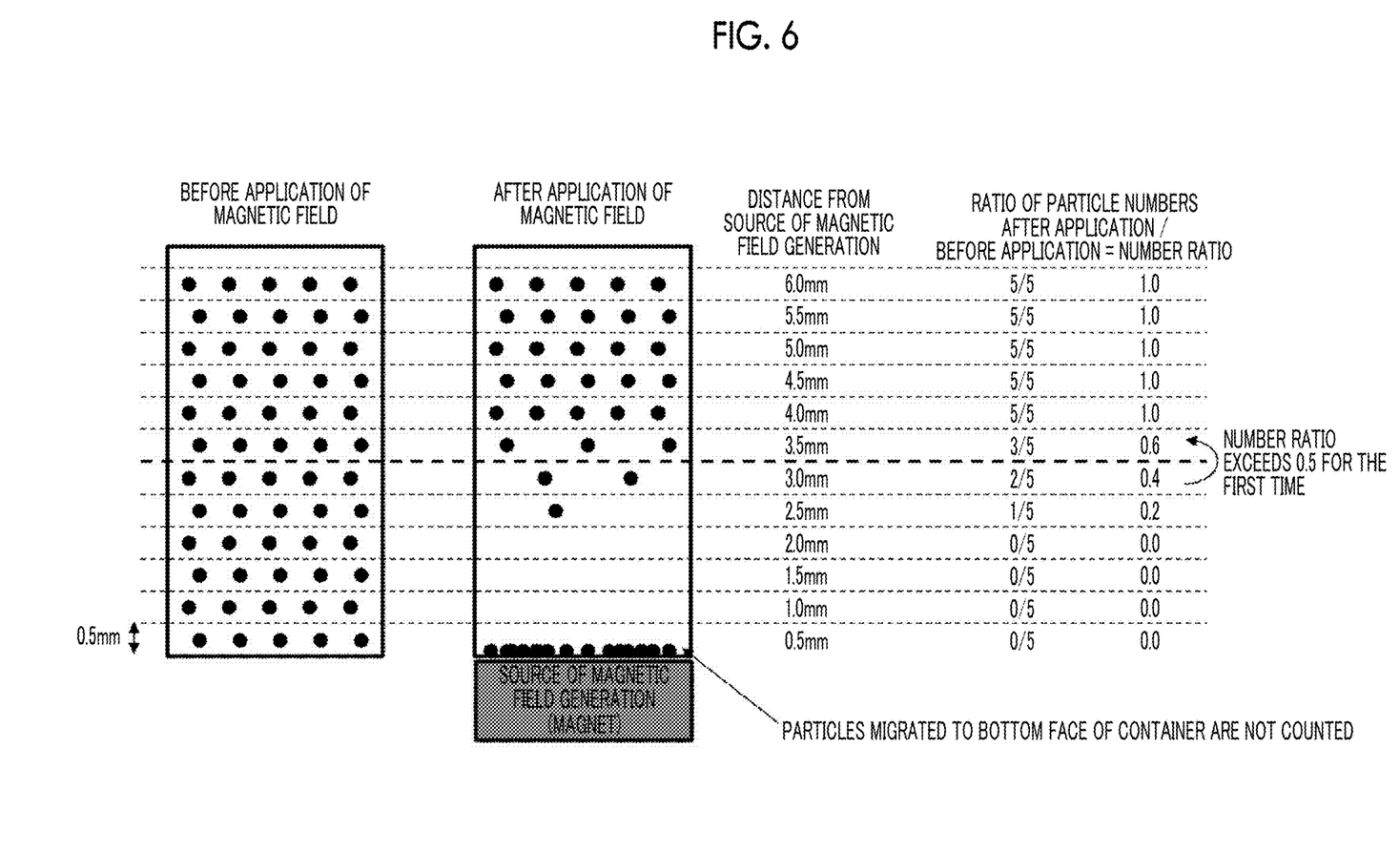
FIG. 6 is an explanatory diagram for explaining an example for the derivation of the ratio of the numbers of magnetic particles existing in the range of a predetermined region according to the second embodiment.

Next, as is the case of the example shown in FIG. 6, for every distance of 0.5 mm from the bottom face 41, that is, in the range of a region five times the diameter of the magnetic particles (an example of the range of the predetermined region of the technology of the present disclosure), the ratio of the particle numbers obtained before and after the application of a magnetic field of the number of magnetic particles 44 existing in that range (after application/before application) is derived for each of the various ranges. The range of the predetermined region is not particularly limited; however, in order to secure the measurement accuracy, a range of 3 or more times and 100 or fewer times the particle size of the magnetic particles is preferred. In a case in which the range of the predetermined region is less than 3 times, the number of times of measurement increases, and also, the range of the predetermined region is narrowed. Thereby, the number of magnetic particles 44 included in the range is decreased, and therefore, the variation tends to increase. On the other hand, in a case in which the range of the predetermined region is more than 100 times, as the range of the predetermined region is widened, the number of the magnetic particles 44 included in the range increases. Therefore, it is difficult to measure the number, and also, the number of plots that will be described below with reference to FIG. 7 is decreased.

For example, in the example shown in FIG. 6, in a case in which the number of the magnetic particles 44 before the application of a magnetic field at a distance x in the range of 2.0 mm or more and less than 2.5 mm is 50, and the number of the magnetic particles 44 after the application of a magnetic field is 10, the ratio of the particle numbers is 0.2. Furthermore, for example, in a case in which the number of the magnetic particles 44 before the application of a magnetic field at a distance x in the range of 2.5 mm or more and less than 3.0 mm is 50, and the number of the magnetic particles 44 after the application of a magnetic field is 20, the ratio of the particle numbers is 0.4.

Figure 7:
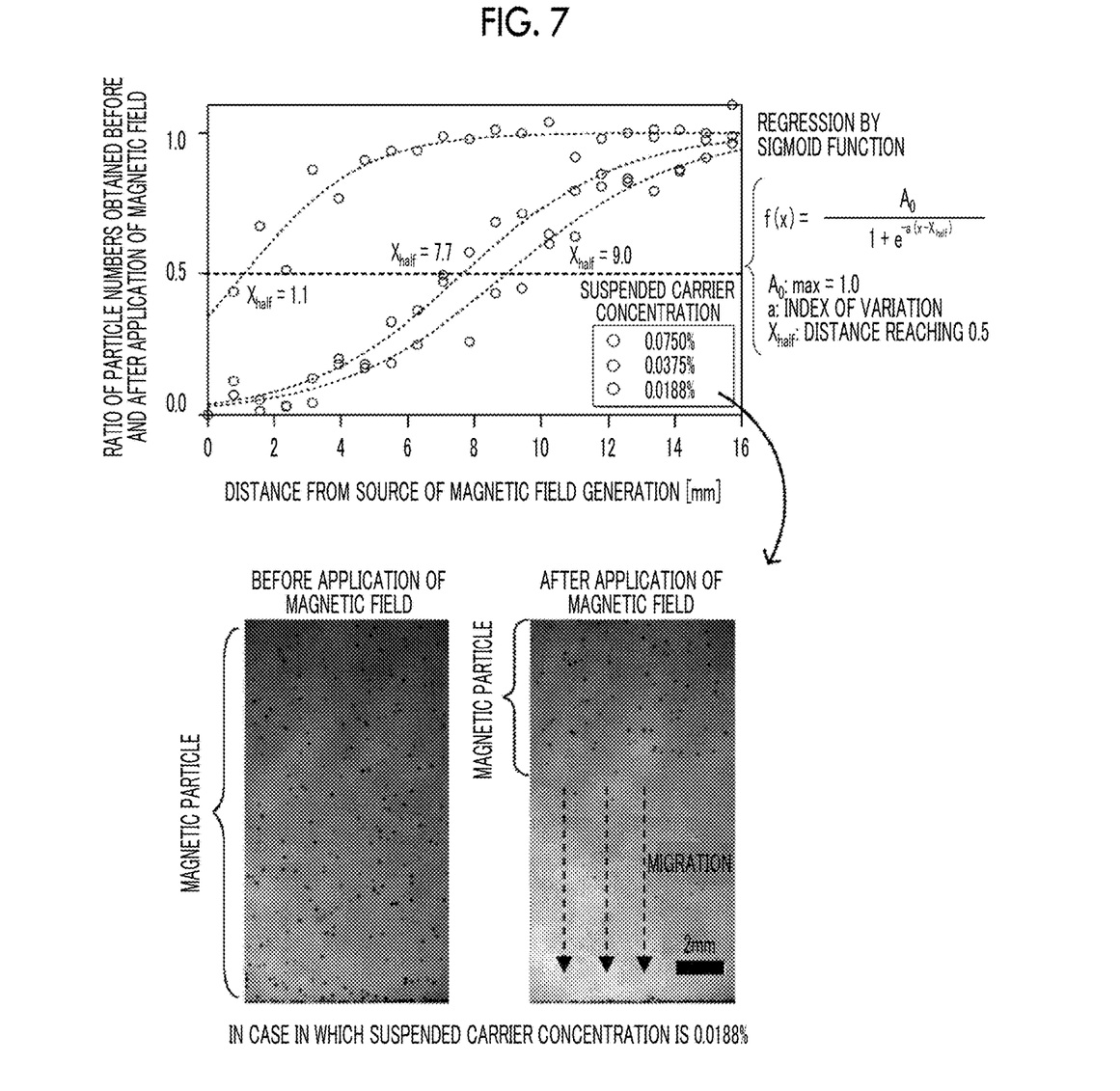
FIG. 7 is a diagram illustrating an example of the correspondence relation between the distance from the bottom face of a container and the ratio of the number of particles before and after the application of a magnetic field, in order to explain the equilibrium distance, $x_{half}$, according to the second embodiment.

After the derivation of the ratio of particle numbers, as shown in the example of FIG. 7, the distance x from the bottom face 41 (magnet 50 as a source of magnetic field generation) of the container 40 is plotted on the axis of abscissa, and the ratio of the particle numbers obtained before and after the application of a magnetic field is plotted on the axis of coordinate. In the example shown in FIG. 7, a case in which an evaluation of three kinds of media having different concentrations of the gel-forming suspended carriers added thereto (Mebiol, cellulose nanofibers, gellan gum, methyl cellulose, and the like) was performed is shown. FIG. 7 shows an example of the state of the magnetic particles 44 being dispersed before and after the application of a magnetic field.

Furthermore, this plot is subjected to fitting a sigmoid function. Specifically, fitting is carried out by the following Formula (1). In Formula (1), the maximum value of $A_0$ is 1.0, and a represents an index value of variations.

$$f(x) = \frac{A_0}{1 + e^{-a(x - x_{half})}} \qquad (1)$$

The value of $x_{half}$ at which the ratio of the particle numbers derived by Formula (1) is 0.5, represents the distance x at which a balance is achieved between the magnetic force and the retention power acting on the magnetic particles 44 in the medium 42 (hereinafter, "equilibrium distance $x_{half}$").

Figure 8:
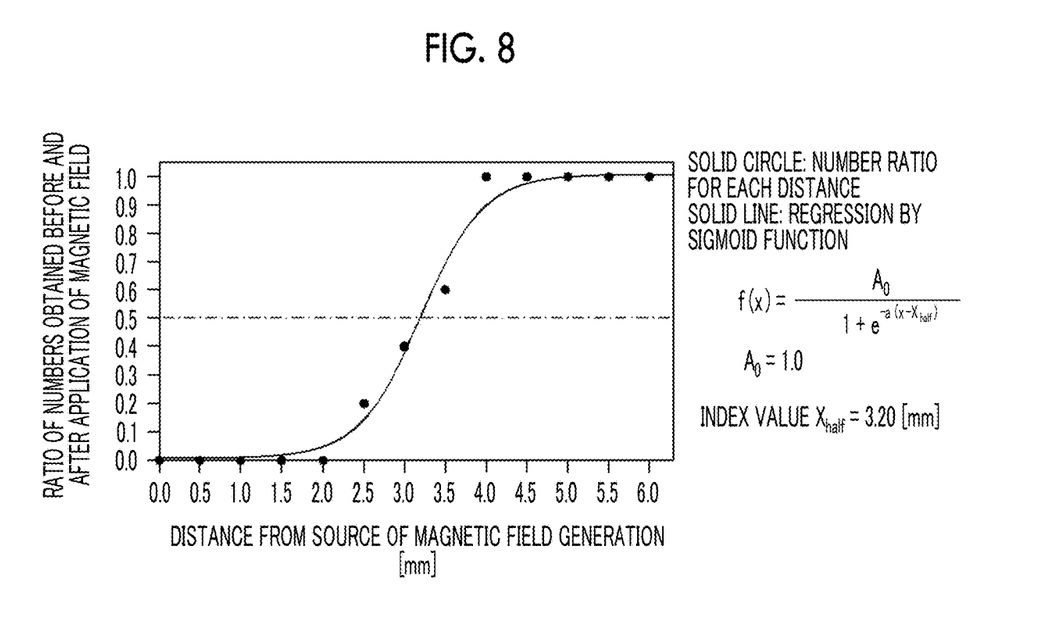
FIG. 8 is a diagram illustrating the correspondence relation between the distance from the bottom face of a container and the ratio of the number of particles before and after the application of a magnetic field, with regard to the equilibrium distance $x_{half}$ in the example illustrated in FIG. 6.

For example, in the case of the example shown in FIG. 6, as shown in FIG. 8, the equilibrium distance $x_{half}$ derived by Formula (1) described above is 3.20 (mm).

In this case, in the subsequent Step S204, the equilibrium distances $x_{half}$ for the measurement of five times are derived and averaged, and the average equilibrium distance $x_{half}$ is used as an index value representing the retention performance of the medium 42. Thereby, the evaluation according to the medium evaluation method of the present embodiment is completed.

Meanwhile, according to a second method, the equilibrium distance $x_{half}$ that serves as an index value representing the retention performance can be simply derived compared to the first method.

In the second method, first, an image analysis is performed for a pair of two images obtained before and after the application of a magnetic field, and the particle number of the magnetic particles 44 retained in the medium 42 excluding the magnetic particles 44 that have settled on the bottom face 41, is counted for each of the images.

Subsequently, the particle number thus counted after the application of a magnetic field is divided by the particle number before the application of a magnetic field, and thereby, the ratio of the particle numbers is derived. Furthermore, a value obtained by multiplying the ratio of the particle numbers thus derived, by the length from the bottom face 41 of the container 40 to the upper limit of the image, is designated as the equilibrium distance $x_{half}$ of the magnetic particles 44.

In this case, in the subsequent Step S204, the equilibrium distances $x_{half}$ for the measurement of five times are derived and averaged, and the average equilibrium distance $x_{half}$ is used as an index value indicating the retention performance of the medium 42. Thereby, the evaluation according to the medium evaluation method of the present embodiment is completed.

Cell aggregates were actually introduced into the medium for which the equilibrium distance $x_{half}$ as an index value for evaluating the suitability of the medium by the above-described evaluation method was obtained, and the retention performance and the recovery efficiency were evaluated. In regard to the retention performance, an evaluation was carried out on the settled state of cells as "floatability" in the same manner as in the first embodiment, and an evaluation was carried out on the fusion or precipitation of cells as "culturing".

Regarding the medium as an object of evaluation, a medium prepared by adding gel-forming suspended carriers (Mebiol, cellulose nanofibers, gellan gum, methyl cellulose, and the like) and a thickening agent to a water-degradable maintenance medium was used. Furthermore, an evaluation was carried out for three kinds of media (media 1, 2, and 3) that included the same components and had no significant differences in viscosity or the like but were produced by different production processes or the like. The concentrations of the components of the media were varied according to the size of the cell aggregates used for the evaluation. In a case in which the size of the cell aggregates was 120 µm or larger, media (media 1, 2, and 3) having high concentrations (composition called Medium 2) were used, and in a case in which the size of the cell aggregates was smaller than the above-described value (80 µm or larger and smaller than 120 µm), media (media 1#, 2#, and 3#) having low concentrations (composition called Medium 1) were used.

The results of performing an evaluation using cell aggregates having a size of 120 µm or larger are presented in Table 4. Furthermore, the results of performing an evaluation using cell aggregates having a size of 80 µm or more and smaller than 120 µm are presented in Table 5.

TABLE 4

| Medium composition | Distance | Evaluation using cells | | |
|---|---|---|---|---|
| Medium 2 | $x_{half}$ [mm] | Floatability | Culturing | Recovery ratio |
| Medium 1 | 5.6 | A | A | A |
| Medium 2 | 0.95 | A | A | B |
| Medium 3 | X | B | B | Z |

TABLE 5

| Medium composition | Distance | Evaluation using cells | | |
|---|---|---|---|---|
| Medium 1 | $x_{half}$ [mm] | Floatability | Culturing | Recovery ratio |
| Medium 1# | 8.7 | A | A | A |
| Medium 2# | 3.4 | A | A | B |
| Medium 3# | X | B | B | Z |

"X" in Table 4 and Table 5 implies that the retention performance of the medium 42 was weak, the magnetic particles 44 settled naturally, and measurement could not be made. "Z" in Table 4 and Table 5 implies that since culture could not be carried out in the medium 42, the recovery ratio could not be evaluated.

Similarly to the first embodiment, in regard to the evaluations of floatability, culturing, and recovery ratio, a case in which a medium was appropriate (highly suitable) for the culture of cell aggregates was rated as "A"; and a case in which a medium was inappropriate (less suitable) for the culture of cell aggregates was rated as "B". Specifically, a medium was rated as "A" or "B" as follows.

In the evaluation of floatability, cell aggregates were dispersed in a medium at a temperature of 37° C., and in a case in which 50% or more of the cell aggregates did not precipitate within 24 hours, the medium was rated as "A", while in a case in which 50% or more of the cell aggregates precipitated, the medium was rated as "B". Here, precipitation means a state in which dispersed cell aggregates have settled at a position of 1 mm or less from the bottom of the container.

In the evaluation of culturing, cell aggregates were cultured in a medium under the conditions of a temperature of 37° C. and 5% of $CO_2$, and in a case in which the cell aggregates had proliferated without undergoing fusion or precipitation until the medium exchange after 48 hours, the medium was rated as "A", while in a case in which fusion or precipitation had occurred, and the cell aggregates did not proliferate, the medium was rated as "B". According to the present embodiment, the "fusion" is a state in which adjacent cell aggregates unite with one another, and whether fusion has occurred was determined by making a microscopic observation. In a case in which five or more fusion products were confirmed in 3 ml of the medium, the medium was rated as "B".

On the occasion of evaluating the recovery ratio, in a case in which the size of the cell aggregates was 80 μm to 120 μm, recovery was carried out by diluting the cell-including medium five times, centrifuging the dilution at 180 g for 3 minutes, and discarding the supernatant. In a case in which the size of the cell aggregates was 120 μm or larger, recovery was carried out by diluting the cell-including medium five times, centrifuging the dilution at 100 g for 3 minutes, and discarding the supernatant.

In regard to the evaluation of the recovery ratio, in a case in which the recovery efficiency (number of cells that could be recovered/total number of cells in the medium) during the recovery of cells was 80% or higher, the medium was rated as "A"; and in a case in which the recovery efficiency was less than 80%, the medium was rated as "B".

As shown in Table 4 and Table 5, media 1 and 1# exhibited satisfactory results in the evaluation of all of floatability, culturing, and recovery ratio ("A"), while media 2 and 2# exhibited satisfactory results in the evaluation of floatability and culturing ("A") but poor results in the evaluation of the recovery ratio ("B"). This is because since the media 2 and 2# have excessively high retention performance, culturing is possible; however, the recovery ratio is low. Meanwhile, media 3 and 3# exhibited poor results in the evaluation of floatability and culturing ("B"). This is because since the media 3 and 3# have poor retention performance, cells could not be cultured, and therefore, in the evaluation of the recovery ratio, the media were rated as "Z".

As can be seen from Table 4 and Table 5, in a case in which a plurality of magnetic particles 44 were dispersed in the medium 42, a magnetic field was applied by disposing a magnet 50 on the bottom face 41 of the container 40, and then the distance of travel x ($X_{half}$) in which the ratio of the numbers of the magnetic particles 44 existing in the range from a position at which the distance of travel from the magnet 50 is the distance of travel x, to the magnet 50, exceeds 0.5 for the first time is measured, a medium having a distance of travel x ($X_{half}$) of from 4 mm to 8 mm can be considered as an adequate medium. The magnetic particles 44 in this case are magnetic particles that use magnetic polylactic acid particles having a particle size of 100 μm, a density of 1.4 g/cm$^3$, and a magnetite percentage content of 40%, and the surface magnetic flux density of the magnet 50 is 200 mT.

As such, according to the medium evaluation method of the present embodiment, the suitability of a medium can be evaluated by using the distance of travel x ($X_{half}$) as an index value. Furthermore, the upper limit of the distance of travel x ($X_{half}$) may be determined in advance based on the retention performance by which the medium retains cell aggregates during culture, and the lower limit of the distance of travel x ($X_{half}$) may be determined in advance based on the recovery efficiency for recovering cell aggregates.

As described above, the medium evaluation method of the present embodiment is a medium evaluation method of evaluating the suitability of a medium for culturing cell aggregates in a suspended state, and the method includes dispersing a plurality of magnetic particles 44 in a medium 42 contained in a container 40, applying a magnetic field thereto, subsequently measuring the distance of travel x ($X_{half}$) in which the ratio of the numbers of magnetic particles 44 existing in the range from a position at which the distance of travel from the magnet 50 as a source of magnetic field generation is the distance of travel x, to the magnet 50, exceeds a predetermined value (0.5) for the first time, and using the distance of travel x ($X_{half}$) thus measured as an index value indicating the suitability of the medium 42.

Thereby, an evaluation of whether a medium is adequate for both the cell retention performance and the cell recovery efficiency is made possible by considering the influence of the network structure formed by the polymers added to the medium.

Furthermore, by culturing cell aggregates by three-dimensional culture using a medium evaluated to be adequate by the medium evaluation method of the present embodiment, culture of cell aggregates can be carried out appropriately.

It is also acceptable to use the medium evaluation method of the first embodiment and the medium evaluation method of the second embodiment in combination.

In this case, for example, it is preferable that a medium exhibiting a sedimentation velocity of 1 mm/s or higher as derived in the medium evaluation method of the first embodiment and exhibiting a distance of travel x ($X_{half}$) of 10 mm or less as derived in the medium evaluation method of the second embodiment, is evaluated to be adequate. For example, it is preferable that a medium exhibiting a sedimentation velocity of from 4 mm/s to 12 mm/s as derived in the medium evaluation method of the first embodiment and exhibiting a distance of travel x ($X_{half}$) of 5 mm or less as derived in the medium evaluation method of the second embodiment, is evaluated to be adequate.

As explained above with reference to Table 2 to Table 5 of the respective embodiments, the evaluation results of the media may vary depending on the size of the cell aggregates. Therefore, the evaluation criteria for the suitability of the medium may be varied depending on the size of the cell aggregates to be cultured. For example, in the case of the first embodiment, in a case in which the cell aggregates in the early stage of culture are small (80 μm or larger and smaller than 120 μm), medium A exhibiting a sedimentation velocity of from 2.5 mm/s to 4.0 mm/s is evaluated as an adequate medium, and culture and recovery of cell aggregates are carried out using medium A. Furthermore, in a case in which the cell aggregates become larger (120 μm or larger), medium B exhibiting a sedimentation velocity of from 1.0 mm/s to 4.0 mm/s is evaluated as an adequate medium, and culture and recovery of cell aggregates are carried out using medium B. By performing evaluation as such, more appropriate retention performance is obtained according to the size of the cell aggregates, and also, culture of the cell aggregates can be appropriately carried out.

In the first embodiment, the sedimentation velocity itself was used as an index value indicating the suitability of a medium; however, other values based on the sedimentation velocity may also be used as the index values. For example, a value obtained by multiplying the sedimentation velocity by a predetermined coefficient may be used as an index value, or the sedimentation velocity may be classified by ranking according to predetermined criteria, and this rank may be used as an index value. Similarly, in the second embodiment, the distance of travel x ($X_{half}$) itself is used as an index value indicating the suitability of a medium; however, other values based on x ($X_{half}$) may also be used as index values. For example, a value obtained by multiplying x ($X_{half}$) by a predetermined coefficient may be used as an index value, or the x ($X_{half}$) may be classified by ranking according to predetermined criteria, and this rank may be used as an index value.

All publications, patent applications, and technical standards mentioned in this specification are herein incorporated by reference to the same extent as if each individual publication, patent application, or technical standard was specifically and individually indicated to be incorporated by reference.

What is claimed is:

1. A medium evaluation method for evaluating suitability of a medium in which cell aggregates are cultured in a suspended state, the method comprising:
dispersing a plurality of magnetic particles in the medium, which is contained in a container;
measuring a distance x in which a number ratio of particle numbers, obtained before and after application of a magnetic field of magnetic particles included in a range of a predetermined region starting at a predetermined distance from a source of magnetic field generation, is a predetermined value; and
using the distance x as an index value indicating the suitability of the medium.

2. The medium evaluation method according to claim 1, wherein the range of the predetermined region is from 3 times to 100 times a particle size of the magnetic particles.

3. The medium evaluation method according to claim 1, wherein magnetic polylactic acid particles having a particle size of 100 μm, a density of 1.4 g/cm$^3$, and a magnetite percentage content of 40% are used as the magnetic particles.

4. The medium evaluation method according to claim 1, wherein the application of the magnetic field is carried out by disposing a magnet having a surface magnetic flux density of from 150 mT to 250 mT on a predetermined unidirectional surface of the container.

5. The medium evaluation method according to claim 1,
magnetic polylactic acid particles having a particle size of 100 μm, a density of 1.4 g/cm$^3$, and a magnetite percentage content of 40% are used as the magnetic particles,
the application of the magnetic field is carried out by disposing a magnet having a surface magnetic flux density of 200 mT on a predetermined unidirectional surface of the container, and
the medium having an index value in a predetermined range is determined to be a suitable medium.

6. The medium evaluation method according to claim 5, wherein an upper limit of the predetermined range is a value that has been predetermined based on a retention performance by which the medium retains the cell aggregates.

7. The medium evaluation method according to claim 5, wherein a lower limit of the predetermined range is a value that has been predetermined based on a recovery efficiency of recovering cell aggregates from the medium.

8. The medium evaluation method according to claim 5, wherein the range of the predetermined region is from 3 times to 100 times the particle size of the magnetic particles.

* * * * *